United States Patent
Telang et al.

(10) Patent No.: US 9,732,076 B2
(45) Date of Patent: Aug. 15, 2017

(54) SOLID ORAL DOSAGE FORMULATION OF HCV INHIBITOR IN THE AMORPHOUS STATE

(71) Applicants: Chitra Telang, Brookfield, CT (US); Zeren Wang, Southbury, CT (US); Li Zhong, New Milford, CT (US)

(72) Inventors: Chitra Telang, Brookfield, CT (US); Zeren Wang, Southbury, CT (US); Li Zhong, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/771,164

(22) PCT Filed: Mar. 13, 2014

(86) PCT No.: PCT/US2014/026028
§ 371 (c)(1),
(2) Date: Aug. 27, 2015

(87) PCT Pub. No.: WO2014/151575
PCT Pub. Date: Sep. 25, 2014

(65) Prior Publication Data
US 2016/0185767 A1    Jun. 30, 2016

Related U.S. Application Data

(60) Provisional application No. 61/791,093, filed on Mar. 15, 2013.

(51) Int. Cl.
| | |
|---|---|
| C07D 417/14 | (2006.01) |
| A61K 9/14 | (2006.01) |
| A61K 9/20 | (2006.01) |
| A61K 31/4709 | (2006.01) |

(52) U.S. Cl.
CPC ............ C07D 417/14 (2013.01); A61K 9/145 (2013.01); A61K 9/2013 (2013.01); A61K 9/2027 (2013.01); A61K 9/2054 (2013.01); A61K 31/4709 (2013.01)

(58) Field of Classification Search
None
See application file for complete search history.

(56) References Cited

U.S. PATENT DOCUMENTS

| | | | |
|---|---|---|---|
| 7,585,845 B2 | 9/2009 | Llinas-Brunet et al. | |
| 8,232,293 B2 * | 7/2012 | Berkenbusch ....... | C07D 417/14 514/312 |
| 2005/0020503 A1 | 1/2005 | Llinas-Brunet et al. | |
| 2007/0218138 A1 | 9/2007 | Bittorf et al. | |
| 2007/0243166 A1 | 10/2007 | Llinas-Brunet et al. | |
| 2010/0093792 A1 | 4/2010 | Berkenbusch et al. | |
| 2011/0160149 A1 * | 6/2011 | Chen ................... | A61K 9/1075 514/21.9 |
| 2011/0177030 A1 | 7/2011 | Llinas-Brunet et al. | |
| 2012/0034187 A1 | 2/2012 | Llinas-Brunet et al. | |
| 2012/0269769 A1 | 10/2012 | Llinas-Brunet et al. | |
| 2012/0270775 A1 | 10/2012 | Berkenbusch et al. | |

FOREIGN PATENT DOCUMENTS

| | | |
|---|---|---|
| WO | 2004103996 A1 | 12/2004 |
| WO | 2005123076 A2 | 12/2005 |

(Continued)

OTHER PUBLICATIONS

International Search Report for corresponding application PCT/US2014/026028, date of mailing Aug. 13, 2014.

(Continued)

*Primary Examiner* — Heidi Reese
(74) *Attorney, Agent, or Firm* — Paula K. Wittmayer; David L. Kershner

(57) ABSTRACT

Described herein are solid oral dosage forms containing Compound (1) or a pharmaceutically acceptable salt thereof (Formula 1), wherein Compound (1) is in the amorphous state. Also described are solid oral dosage forms comprising a composition of Compound (1) in the amorphous state and one or more pharmaceutically acceptable excipients. Compound (1) is a specific inhibitor of the hepatitis C virus (HCV) NS3/4A serine protease. Thus, also described herein are methods for using the described solid oral dosage forms in the treatment of HCV infection. Also described are processes for the manufacture of the solid oral dosage forms.

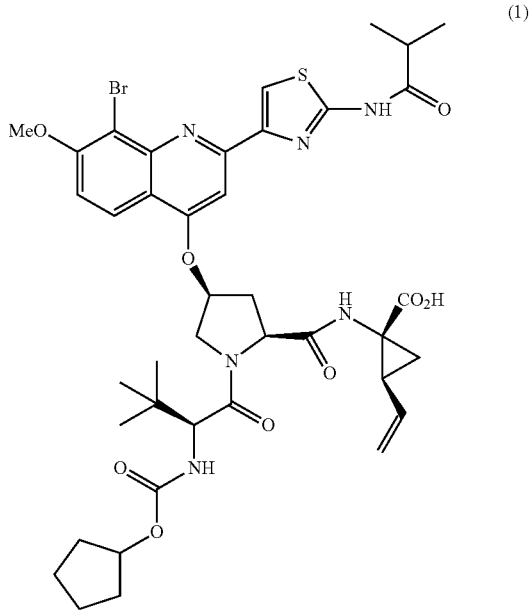

19 Claims, 2 Drawing Sheets

(56) References Cited

FOREIGN PATENT DOCUMENTS

| WO | 2009050289 | A2 | 4/2009 |
| WO | 2010033444 | A1 | 3/2010 |
| WO | 2011005646 | A2 | 1/2011 |
| WO | 2011156578 | A1 | 12/2011 |
| WO | 2013101550 | A1 | 7/2013 |

OTHER PUBLICATIONS

Vachon et al., BI-201335 treatment of Hepatitis C Virus Serine Protease NS3/Non-Structural Protein 4A (NS4A) Inhibitor, Drugs of the Future, vol. 37, No. 2, Feb. 2012, pp. 99-109.

* cited by examiner

SOLID ORAL DOSAGE FORMULATION OF HCV INHIBITOR IN THE AMORPHOUS STATE

FIELD OF THE INVENTION

The present invention relates in general to solid oral dosage formulations of a potent HCV inhibitor, where the inhibitor is present in the formulation in the amorphous state, methods of using this formulation for the inhibition of HCV replication and the treatment of HCV infection.

BACKGROUND OF THE INVENTION

The following Compound (1):

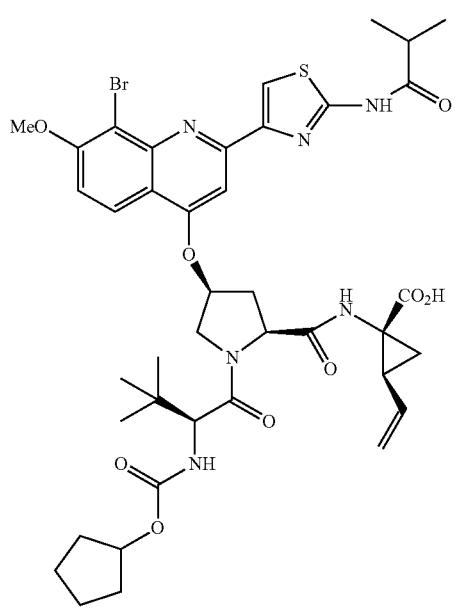

(1)

(hereinafter "Compound (1)"), also known as faldaprevir, is known as a potent and selective inhibitor of HCV NS3 serine protease and falls within the scope of the acyclic peptide series of HCV inhibitors disclosed in U.S. Pat. Nos. RE 40,525, 7,514,557 and 7,585,845. Compound (1) is disclosed specifically as Compound #1055 in U.S. Pat. No. 7,585,845, and as Compound #1008 in U.S. Pat. No. 7,514,557. Preferred forms of Compound (1) include the crystalline forms, in particular the crystalline sodium salt form as described in U.S. Pat. No. 8,232,293. Compound (1), including the pharmaceutically acceptable salt forms thereof such as the sodium salt form, can be prepared according to the general procedures found in the above-cited references, all of which are herein incorporated by reference.

Compound (1) may also be known by the following alternate depiction of its chemical structure, which is equivalent to the above-described structure:

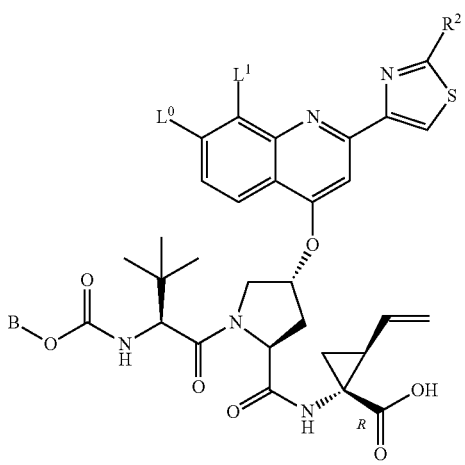

wherein B is

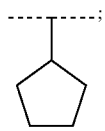

$L^0$ is MeO—; $L^1$ is Br; and $R^2$ is

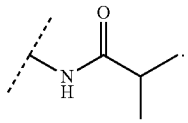

An existing formulation containing Compound (1) is a product in the form of a self-emulsifying drug delivery system (SEDDS) composition. The known SEDDS composition comprises a lipid-based pharmaceutical composition of the active suitable for oral administration via a liquid-filled capsule, and in particular a softgel capsule (see US Application Publication US 2011/0160149).

A disadvantage of these liquid SEDDS formulations is a propensity to form a specific genotoxic degradation product (hereinafter referred to as "Compound X.") Compound X may be depicted by the following chemical structure showing the stereochemistry at the two chiral centers in this molecule:

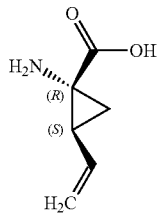

Due to the high potential toxicity of the Compound X, the increase in this impurity over the product shelf life duration was deemed unacceptable from a regulatory perspective and thus there was an urgent need to solve this problem. For example, the EMEA (European Medicines Agency) Guideline on the Limits of Genotoxic Impurities (28 Jun. 2006) specifies a maximum intake value of 1.5 μg/day of a genotoxic impurity as being associated with an acceptable risk (1 in 100,000 increased cancer risk) for most marketed pharmaceuticals based on a lifetime exposure duration. For short duration treatment regimens higher levels of genotoxic impurities may be acceptable based on application of Haber's rule (fundamental concept in toxicology) to extrapolate acceptable limits for daily intake for shorter treatment durations (Fetter et al, Critical Reviews in Toxicology, 2011) without changing the associated level of cancer risk. For example, in its subsequent guidance document issued on 26 Jun. 2008, the EMEA's CHMP Safety Working Party indicated that the acceptable limits for daily intake of genotoxic impurities during clinical trials (1 in 1 million increased cancer risk plus an additional dose rate correction factor of 2) are 5, 10, 20, and 60 μg/day for a duration of exposure of 6-12 months, 3-6 months, 1-3 months, and less than 1 month, respectively. Since the treatment regimen with Compound (1) may be as short as 12 weeks (~3 months) or 24 weeks (~6 months), maximum allowable intake values for Compound X may be as high as 20 μg/day (3 month regimen) or 10 μg/day (6 month regimen) when applying a 1 in 1 million increased cancer risk and a dose rate correction factor of 2. Taking into consideration the benefit of an approved marketed product, the maximum allowable intake values for Compound X may be as high as the calculated acceptable limit of 400 μg/day (3 month regimen) or 200 μg/day (6 month regimen) when applying a 1 in 100,000 increased cancer risk level. Thus, one goal of the present invention was to develop techniques to ensure that the maximum intake value of this degradation product would be maintained below these regulatory limits.

Prior to the discovery that Compound X was an Ames positive degradation product, the stability of Compound (1) NA drug products was controlled by standard product packaging (HDPE bottle with induction seal) and room temperature storage. Such conditions were considered sufficient to allow for the desired commercial product shelf life. As noted above, current regulatory requirements for controlling potentially genotoxic impurities limit such impurities to levels much lower than standard impurities. The discovery that Compound X was Ames positive and genotoxic required the development of further controls to insure the lowest possible levels of Compound X in the drug product for patient safety and to meet requirements of regulatory authorities.

While the level of the degradation product can be lessened by refrigerated storage of the liquid SEDDS product, such storage has its own cost and logistics disadvantages. The liquid form is also disadvantageous due to higher complexity in manufacture and due to the need to contain the liquid, such as by a capsule.

A solid dosage form is more preferred for manufacturing and product stability in transportation and storage.

SUMMARY OF THE INVENTION

The present invention overcomes the aforementioned problems attendant with the existing liquid formulation by providing a new solid oral dosage composition of a potent HCV inhibitor, where the inhibitor is present in the composition in the amorphous state. The formulations of the invention provide the dissolution and bioavailability advantages of the active being in amorphous form while avoiding the disadvantages of a liquid formulation, and also have improved stability as compared to liquid formulations with respect to formation of a degradation by-product. In one embodiment of the invention, the compositions of the invention comprise Compound (1) or a pharmaceutically acceptable salt thereof in the amorphous state together with either a water-soluble base or a hydrophilic, solid dispersion-forming polymer, or both the base and polymer. In another embodiment of the invention, the compositions of the invention comprise a pharmaceutically acceptable salt of Compound (1) in the amorphous state. The compositions of either of these embodiments may also optionally contain a surfactant, and optionally one or more additional excipients or additives as described in more detail below.

DETAILED DESCRIPTION OF THE INVENTION

Definitions of Terms

Figure 1:
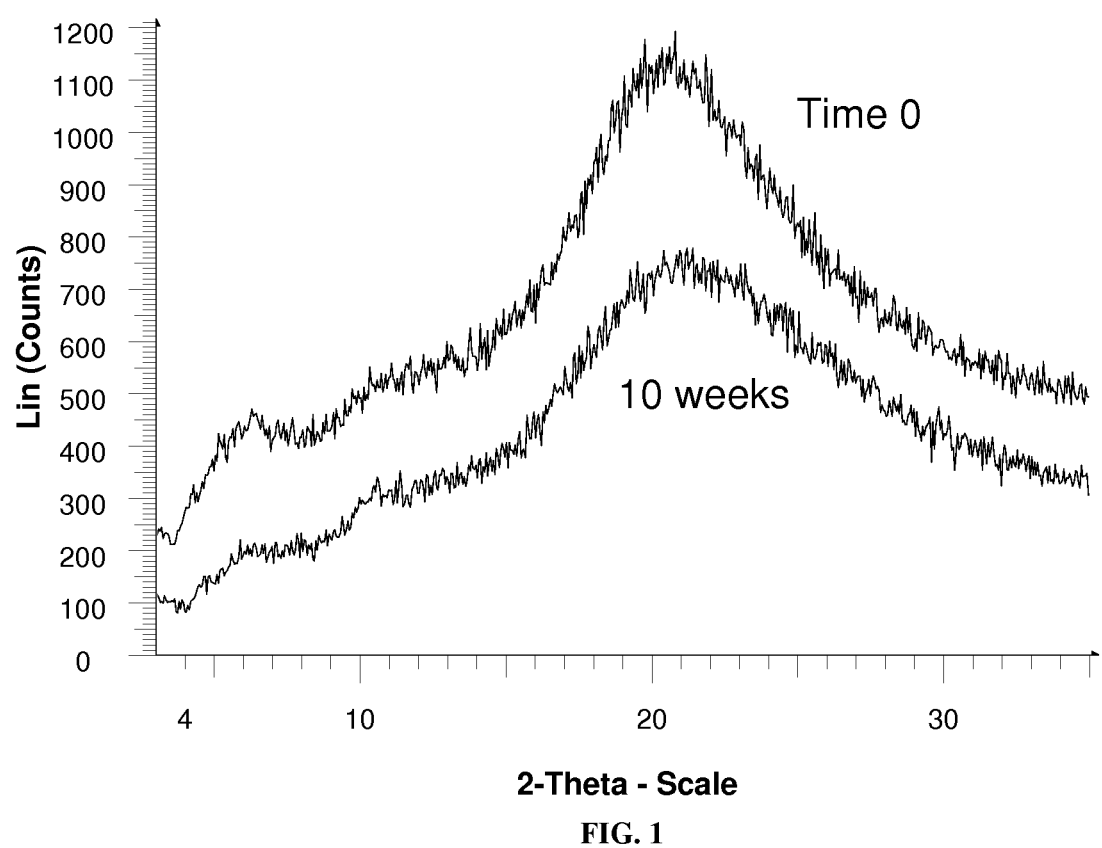
FIG. 1 shows the XRPD patterns of an amorphous sodium salt of Compound (1) present as a solid dispersion with arginine in 1:1 proportion by weight over 10 weeks under accelerated storage (50° C./ambient RH).

Terms not specifically defined herein should be given the meanings that would be given to them by one of skill in the art in light of the disclosure and the context. As used throughout the present application, however, unless specified to the contrary, the following terms have the meaning indicated:

The term "Compound (1)" as used herein is intended to encompass all pharmaceutically acceptable salts of Compound (1) unless the context indicates otherwise.

The term "active" as used herein is intended to encompass Compound (1) and all pharmaceutically acceptable salts of Compound (1) unless the context indicates otherwise.

The term "about" as used herein means within 5%, and more preferably within 1%, of a given value or range. For example, "about 3.7%" means from 3.5 to 3.9%, preferably from 3.66 to 3.74%. When the term "about" is associated with a range of values, e.g., "about X % to Y %", the term "about" is intended to modify both the lower (X) and upper (Y) values of the recited range. For example, "about 20% to 40%" is equivalent to "about 20% to about 40%".

The term "treating" with respect to the treatment of a disease-state in a patient include
 (i) inhibiting or ameliorating the disease-state in a patient, e.g., arresting or slowing its development; or
 (ii) relieving the disease-state in a patient, i.e., causing regression or cure of the disease-state. In the case of HCV, treatment includes reducing the level of HCV viral load in a patient.

The term "storage stable" as used herein is intended to refer to compositions which control formation of Compound X to reduced levels below regulatory accepted limits under accelerated temperature/RH conditions (25° C./60% RH, 30° C./70% RH).

The term "pharmaceutically acceptable" with respect to a substance as used herein means that substance which is, within the scope of sound medical judgment, suitable for use in contact with the tissues of humans and lower animals without undue toxicity, irritation, allergic response, and the like, commensurate with a reasonable benefit/risk ratio, and effective for the intended use when the substance is used in a pharmaceutical composition.

The term "pharmaceutically acceptable salt" means a salt of a compound (1) which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, e.g., S. M. Birge et al., J. Pharm. ScL, 1977, 66, pp. 1-19 and U.S. Pat. No. 7,585,845. The various salts listed in U.S. Pat. No. 7,585,845 are herein incorporated by reference. A particularly preferred form of Compound (1) to be used in the composition of the present invention is the sodium salt form of Compound (1).

All percentages by weight in the compositions are percentages by weight with respect to the whole composition.

Embodiments of the Invention

The invention provides a solid oral dosage composition comprising a pharmaceutically acceptable salt of Compound (1) in the amorphous state. In a preferred embodiment, the compositions comprise a sodium salt of Compound (1) in the amorphous state.

The invention further provides a solid oral dosage composition comprising:
  the active, in the amorphous state,
  a water-soluble base or
  a hydrophilic, solid dispersion-forming polymer, or
  both a water-soluble base and a hydrophilic, solid dispersion-forming polymer.

The compositions/formulations of the invention provide the active in an amorphous form and provide that the active can be stably maintained in an amorphous form. Providing the active in an amorphous form is advantageous for its pharmaceutical use. The active naturally has lipophilic/hydrophobic properties which lead to disadvantages in dissolution and bioavailability. The amorphous form of the active has better dissolution properties than crystalline forms in an aqueous medium and, thus, improved bioavailability upon administration to a patient.

The formulations described are also advantageous because they are in solid form, e.g., in the form of a tablet or a powder, e.g., a powder in a capsule. The previously known compositions for the active had the active in a liquid form contained in a soft-gel capsule. Providing the active in the liquid form was advantageous for its dissolution upon administration. However, it had been discovered that this liquid form was prone to degradation to a genotoxic degradation product. The degradation was enhanced by temperature, even at room temperature, thus, creating the necessity to refrigerate the liquid in soft-gel formulations. The degradation was also enhanced by humidity which was particularly disadvantageous because the soft-gel formulations required maintaining some humidity to prevent drying out of the gel capsule. The formulations described herein provide solid compositions wherein the active is maintained in amorphous form. Thus the formulations provide the dissolution and bioavailability advantages of the active being in amorphous form while avoiding the disadvantages of active being in a liquid form.

When the formulations contain a water-soluble base, this basifying agent stabilizes the active against degradation to the genotoxic product. While not intending to be bound by this theory, it is theorized that the base creates a favorable basic microenvironment which stabilizes the active against acid hydrolysis which leads to the genotoxic degradation product.

The basifying agent is a water-soluble base which is pharmaceutically acceptable. Preferred bases include arginine, tromethamine (i.e., tris(hydroxymethyl)aminomethane), meglumine, carbonate buffer and sodium carbonate. In one preferred embodiment, the base is arginine. In another preferred embodiment, the base is provided in a form such that it amorphizes in the composition to provide a basic microenvironment which prevents acid hydrolysis of the active, e.g., arginine and tromethamine. It has been discovered that arginine, although it is normally crystalline, can be amorphized in compositions with the active and thus can be provided as an amorphous solid dispersion in the compositions to provide a basic microenvironment. Thus, in one embodiment the water-soluble base is an amorphous solid dispersion with the Compound (1) in the amorphous state.

The base is preferably provided in a weight ratio of active to base ranging from about 1:1 to 10:1, preferably about 1:1 to 7:3. The base can be incorporated in the composition, for example, by spray drying, wet granulation, dry granulation, coprecipitation or extrusion.

When the composition contains a hydrophilic, solid dispersion-forming polymer the polymer counter-balances the drug's lipophilicity and improves drug dissolution. This leads to enhanced dissolution even when a surfactant is not incorporated into the composition. The polymer can even provide for supersaturation of the active in the composition. Preferred polymers for this purpose are PVP (polyvinylpyrrolidones) and its copolymers, such as polyvinylpyrrolidone/polyvinylacetic acid, and cellulosic polymers such as HPMC and its derivatives.

The polymer is preferably provided in the composition in a weight ratio of about 1:0.1 to 1:10 (active:polymer) relative to the total composition.

Following are examples of four types of embodiments of the form of the compositions:

I. The first form, hereinafter "Type I", is a solid composition which contains:
  Compound (1) in the amorphous state; a water-soluble base; and one or more pharmaceutically acceptable excipients.

II. The second form, hereinafter "Type II", contains the Compound (1) in amorphous form dispersed in a polymer. The polymer is a hydrophilic, solid dispersion-forming polymer.

III. The third form, hereinafter "Type III", combines Compound (1) in the amorphous state with both the base and polymer components of Type I and II.

IV. The fourth form, hereinafter "Type IV", contains Compound (1) as a pharmaceutically acceptable salt, preferably sodium salt, in the amorphous form.

The compositions of the invention can be advantageous in their ability to control the formation of undesired degradation product (Compound X) and therefore are able to markedly improve stability. For example, the use of basification in the solid dispersion compositions Types I and III is advantageous for this purpose. In composition Types I and III, a water soluble base is incorporated in the amorphous solid dispersion to afford microenvironmental pH advantage.

In any of the embodiments of the invention, the composition may contain a surfactant. The surfactant aids in dispersing the components in the composition. For example, in the embodiments where the amorphous active Compound (1) is an amorphous solid dispersion dispersed in a polymer, the surfactant aids in dispersing the active at the molecular scale in the polymer. The enhancement of dispersion is advantageous for improving the dissolution of the active in an aqueous medium, e.g., upon administration to a patient. Preferred as surfactants are anionic surfactants, such as those based on sulfate, sulfonate, phosphate or carboxylate anions. Examples of the sulfate anionic surfactants are: alkyl sulfates, such as, sodium lauryl sulfate (also known as sodium dodecyl sulfate or SDS), and ammonium lauryl sulfate; alkyl ether sulfates, such as, sodium laureth sulfate (SLES) and sodium myreth sulfate; sulfonates, such as, docusates (e.g., dioctyl sodium sulfosuccinate), sulfonate fluorosurfactants (e.g., perfluorooctanesulfonate (PFOS) and perfluorobutanesulfonate); and, alkyl benzene sulfonates; phosphates, such as alkyl aryl ether phosphates and alkyl ether phosphates; and carboxylates, such as, alkyl carboxylates (e.g., fatty acid salts, such as sodium stearate), sodium lauroyl sarcosinate, and carboxylate fluorosurfactants (e.g., perfluorononanoate and perfluorooctanoate (PFOA or PFO)).

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The pharmaceutical compositions of this invention may be orally administered in any orally acceptable dosage form including, but not limited to, capsules and tablets. In the case of tablets for oral use, carriers which are commonly used include lactose and corn starch. Lubricating agents, such as magnesium stearate, are also typically added. For oral administration in a capsule form, useful diluents include lactose and dried corn starch. Other suitable vehicles or carriers for the above noted formulations and compositions can be found in standard pharmaceutical texts, e.g. in "Remington's Pharmaceutical Sciences", The Science and Practice of Pharmacy, 19$^{th}$ Ed. Mack Publishing Company, Easton, Pa., (1995).

Methods of Preparation

Formulations according to the invention can be made, for example, by utilizing the active as an amorphous solid or an amorphous solid dispersion which, for example, can be prepared by spray-drying. The combined steps of granulation, blending and tableting can then be used to make the final pharmaceutical formulation. For example, the active as an amorphous solid or an amorphous solid dispersion is granulated together with intragranular components. Any additional extragranular components may then be blended. The blended components can then be pressed into tablets of a desired hardness or can be used in powder form.

Characteristics of the Compositions

The compositions/formulations of the invention provide the active in an amorphous form and provide that the active can be stably maintained in an amorphous form. Providing the active in an amorphous form is advantageous for its pharmaceutical use. The active naturally has lipophilic/hydrophobic properties which lead to disadvantages in dissolution and bioavailability. The amorphous form of the active has better dissolution properties than crystalline forms in an aqueous medium and, thus, is predicted to have improved bioavailability upon administration to a patient.

The formulations described are also advantageous because they are in solid form, e.g., in the form of a tablet or a powder. The previously known compositions for the active had the active in a liquid form contained in a soft-gel capsule. The formulations described herein provide solid compositions wherein the active is maintained in amorphous form. Thus the formulations provide the dissolution and bioavailability advantages of the active being in amorphous form while avoiding the disadvantages of active being in a liquid form.

Other advantages that are achievable with the compositions of the present invention include the lack of temperature dependence on the formation of the above-discussed genotoxic degradation product, which may allow avoiding the use of refrigerated storage. Another advantage is a faster dissolution rate. For example, the compositions which contain the base have higher solubility in basic pH since along with the active, a highly water soluble base, such as arginine, will selectively dissolve. In an amorphous solid dispersion state in the formulation, the water soluble base is able to produce a basic environment and enhance dissolution of the active.

The compositions containing the base can successfully disperse a hydrophobic drug, for example, to a molecular level, with a highly water-soluble base to resolve both physical and chemical stability issues. The base will retain its amorphous form in the compositions even when they are formulated into solid form. As explained above, the genotoxic degradant Compound X has been identified in long term stability studies on a capsule formulation. The acceptable level of this degradant is in the order of ppm levels. However, it can be generated through degradation, for example, via interaction with lipid based liquid excipients which are used in soft-gel capsule formulations. The approach of molecular mixing with a water-soluble base as provided herein maintains a basic local pH through the amorphous fraction of tablet and is able to control the formation of degradation product, for example, down to ppm levels, particularly less than 15 ppm, more particularly less than 6 ppm. In terms of concentration of Compound X in formulations, for example, when a full daily dose is 240 mg of Compound (1), this intake value (1.5 µg/day) calculates to a level of 6 ppm (parts-per-million). Thus, an additional embodiment is wherein the resulting amount of degradation product X in the composition is below a level of about 6 ppm for each 240 mg of Compound (1) or pharmaceutically acceptable salt thereof. Preferred sub-embodiments at such dosage include upper limits of 3 ppm, or 2 ppm or 1 ppm. As an additional example, when a full daily dose is 120 mg of Compound (1), this intake value (1.5 µg/day) calculates to a level of 12 ppm (parts-per-million). Thus, an additional embodiment is wherein the resulting amount of degradation product X in the composition is below a level of about 12 ppm for each 120 mg of Compound (1) or pharmaceutically acceptable salt thereof. Preferred sub-embodiments at such dosage include upper limits of 8 ppm, or 4 ppm or 2 ppm. Further preferably, the maximum allowable intake values for Compound X may be as high as the calculated acceptable limit of 400 µg/day (3 month regimen) or 200 µg/day (6 month regimen) when applying a 1 in 100,000 increased cancer risk level. Thus, one goal of the present invention was to develop techniques to ensure that the maximum intake value of this degradation product would be maintained below regulatory limits.

Despite the addition of the base, such as an arginine, in a weight fraction less than the active in the amorphous fraction of the tablet, the dispersion is stable to crystallization even without a polymer. A major advantage gained with tablet manufacturing is the ability to manufacture and store tablets in 'near dry' conditions (whereas a certain minimum level of water is necessary for soft-gelatin dosage forms). Since this is a hydrolytic degradant, the ability for such dry processing further helps to control this impurity.

The compositions of the invention provide Compound (1) in a physically stable form. It has been discovered that Compound (1) is advantageous for carrying out this invention based on its ability to be physically stable in the amorphous form due to its unexpectedly very high glass transition temperature (Tg). This reduces molecular mobility significantly and helps to off-set the lowering of Tg in a solid dispersion with an excipient that would, otherwise, be readily crystallizable. The base arginine, for example, is not normally amorphized readily and has a very low Tg. The amorphous form of Compound (1) here, however, is able to disperse arginine in an amorphous and molecularly mixed state without the active crystallizing out. Based on exposure tests below (see Examples 2-3) exposure is severely compromised when the active is in crystalline form.

The compositions of the invention containing the base also provide Compound (1) in a chemically stable form. In the intimately mixed form, the water soluble base is able to create a favorable basic microenvironment to stabilize the active against acidic hydrolysis and limit the amount of degradation product formed even under accelerated storage temperatures, leading to a potentially stable product at room temperature.

It has also been found advantageous to control moisture to minimize hydrolysis. Moisture content plays a key role in accelerating the degradation. Unlike softgel capsules which require a certain threshold of water to maintain their integrity, solid forms, such as tablets, can be stored under 100% desiccation without concerns of over-drying. Thereby, such storage conditions can be utilized with the solid forms described herein, thereby controlling formation of the genotoxic degradant more effectively. This can be done successfully by manufacturing under a controlled 15% RH environment in isolators. This can result in a drop in moisture content from ~4% to <2%. Moreover, a continued water loss/drying during storage when under such storage conditions can be observed, for example, about 1.8% to 1%.

According to an alternate embodiment, the pharmaceutical compositions of this invention may additionally comprise another anti-HCV agent. Examples of other anti-HCV agents include, α- or β-interferon, ribavirin, amantadine and telaprevir.

According to another alternate embodiment, the pharmaceutical compositions of this invention may additionally comprise other inhibitors of HCV protease.

According to yet another alternate embodiment, the pharmaceutical compositions of this invention may additionally comprise an inhibitor of other targets in the HCV life cycle, including but not limited to, helicase, polymerase, metalloprotease or internal ribosome entry site (IRES).

Methods of Therapeutic Use

The Compounds of formula (1) are effective as HCV protease inhibitors, and these compounds and pharmaceutical compositions comprising these compounds are therefore useful in inhibiting the replication of HCV and in the treatment of HCV infection in a mammal. Therefore, the present invention is also directed to treating a hepatitis C viral infection in a mammal by administering to the mammal a therapeutically effective amount of a pharmaceutical composition of the present invention.

Dosage levels of the Compounds of formula (1) and various treatment regimens in the monotherapy for the prevention and treatment of HCV infection are as set forth in U.S. Pat. No. 7,585,845. As the skilled artisan will appreciate, however, lower dosages may be possible with the compositions of the present invention depending on the level of improvement in bioavailability. Combination therapy is also possible with one or more additional therapeutic or prophylactic agents as fully described by U.S. Pat. No. 7,585,845. The additional agent(s) may be combined with the compounds of this invention to create a single dosage form or, alternatively, these additional agent(s) may be separately administered to a mammal as part of a multiple dosage form. An appropriate therapeutically effective amount of the pharmaceutical composition to be administered can be determined routinely by one of ordinary skill in the art having regard to their own knowledge, the prior art, and this disclosure.

In order that this invention be more fully understood, the following examples of are set forth. These examples are for the purpose of illustrating embodiments of this invention, and are not to be construed as limiting the scope of the invention in any way.

EXAMPLES

In all the exemplified formulations, the active, Compound (1), was contained in an amount of 120 mg.

Tablets Preparation for Formulation A-E:

Prototype tablets were manufactured at bench scale using an immediate release amorphous or crystalline tablet formulation and a dry-granulation process. The amorphous Compound (1) sodium salt is prepared by dissolving the active in the organic solvent and then spray drying at a chosen inlet temperature and atomizer speed. The crystalline Compound (1) sodium salt may be prepared as described in U.S. Pat. No. 8,232,293. Excipients were blended with the active successively first as intragranular and then as extragranular components. Lubricant was then added and the mixture compressed into tablets.

TABLE 1

(Comparison Formulation - Crystalline Tablet)
Formulation A. 120 mg Crystalline Drug Tablet Formulation

| Component | Amount (wt %) |
|---|---|
| Crystalline drug - Compound (1) sodium salt | 21.8 |
| SDS | 9.1 |
| L-arginine (crystalline, physically mixed) | 9.1 |
| Avicel PH101 | 23.5 |
| Lactose Monohydrate regular | 23.5 |
| Ac-Di-Sol | 5.6 |
| Cab-O-Sil | 0.5 |
| Magnesium stearate | 0.2 |
| Extragranular Components | |
| Ac-Di-Sol | 6 |
| Cab-O-Sil | 0.5 |
| Magnesium stearate | 0.3 |
| Tablet Characteristics | |
| Tablet weight (mg) | 550 |

TABLE 2

(Comparision Formulation - Crystalline Tablet)
Formulation B. 120 mg Enteric-Coated Crystalline Drug Tablet

| Component | Amount(wt %) |
|---|---|
| Crystalline drug - Compound (1) sodium salt | 21.8 |
| SDS | 9.1 |

TABLE 2-continued (Comparision Formulation - Crystalline Tablet)
Formulation B. 120 mg Enteric-Coated Crystalline Drug Tablet

| | Amount(wt %) |
|---|---|
| L-arginine | 9.1 |
| Avicel PH101 | 23.5 |
| Lactose Monohydrate regular | 23.5 |
| Ac-Di-Sol | 5.6 |
| Cab-O-Sil | 0.5 |
| Magnesium stearate | 0.2 |
| *Extragranular Components* | |
| Ac-Di-Sol | 6 |
| Cab-O-Sil | 0.5 |
| Magnesium stearate | 0.3 |
| *Tablet Characteristics* | |
| Tablet weight (mg) | 550 |
| *Coatings* | |
| HPMC(Methocel E5 Prem) seal coat | 2.1 |
| 10:1 Eudragit L30D55:TEC enteric coating | 2.1 |
| Final Coated Tablet Weight | 573 |

TABLE 3

(Type I Formulation)
Formulation C. 120 mg Amorphous Drug Tablet Formulation

| Component | Amount (wt %) |
|---|---|
| Amorphous drug - Compound (1) sodium salt | 21.8 |
| SDS | 9.1 |
| L-arginine (crystalline, physically mixed) | 9.1 |
| Avicel PH101 | 23.5 |
| Lactose Monohydrate regular | 23.5 |
| Ac-Di-Sol | 5.6 |
| Cab-O-Sil | 0.5 |
| Magnesium stearate | 0.2 |
| *Extragranular Components* | |
| Ac-Di-Sol | 6 |
| Cab-O-Sil | 0.5 |
| Magnesium stearate | 0.3 |
| *Tablet Characteristics* | |
| Tablet weight (mg) | 550 |

TABLE 4

(Type II Formulation)
Formulation D. 120 mg 50% Compound (1) sodium salt in hydroxyproply-methylcellulose (HPMCAS) polymer solid dispersion Tablet Formulation

| Component | Amount (wt %) |
|---|---|
| Amorphous Compound (1) Na salt | 21.8 |
| HPMCAS polymer | 21.8 |
| Avicel PH101 | 24.5 |
| Lactose Monohydrate regular | 24.5 |
| Ac-Di-Sol | 6 |
| Cab-O-Sil | 0.5 |
| Magnesium stearate | 0.25 |
| *Extragranular Components* | |
| Cab-O-Sil | 0.5 |
| Magnesium stearate | 0.25 |
| *Tablet Characteristics* | |
| Tablet weight (mg) | 550 |

TABLE 5

(Type II Formulation)
Formulation E. 75% (Compound (1))/25% PVP-K30 amorphous solid dispersion (SDD) Tablet with SDS Formulation

| Component | Amount (wt %) |
|---|---|
| Amorphous (Compound (1) Na salt | 21.8 |
| PVP-K30 polymer | 7.3 |
| SDS | 9.1 |
| Avicel PH101 | 24.4 |
| Lactose Monohydrate regular | 24.4 |
| Ac-Di-Sol | 5.6 |
| Cab-O-Sil | 0.5 |
| Magnesium stearate | 0.25 |
| *Extragranular Components* | |
| Ac-Di-Sol | 6 |
| Cab-O-Sil | 0.5 |
| Magnesium stearate | 0.25 |
| *Tablet Characteristics* | |
| Tablet weight (mg) | 550 |

TABLE 6

(Comparison Formulation - known softgel form capsule)
The below softgel capsules may be prepared as described in U.S. Patent Application Publication No. 2011/0160149.
Formulation F. 120 mg liquid drug in softgel capsule

| Component | Amount (wt %) |
|---|---|
| Compound (1) - sodium salt, liquid form | 15 |
| Mono-, diglycerides of Caryl/Capric Acid (Capmul MCM) | 46.3 |
| Polyoxyl 35 Castor Oil (Cremophor EL) | 30.8 |
| Propylene Glycol (PG) | 7.7 |
| DL-α-tocopherol | 0.2 |
| Total Fill ( mg) | 800 |

Example 1

The attached FIG. 1 shows the XRPD patterns of (1:1) amorphous Compound (1)/arginine solid dispersion over 10 weeks under accelerated storage. The top line shows the initial XRPD pattern and the bottom line the pattern after 10 weeks. The XRPD data demonstrates the physical stability for this composition according to the invention. X-ray powder diffraction studies were conducted using a Bruker D8 Advance with Gobel mirror in parallel beam geometry. Scans were conducted from 3 to 35° (degrees 2θ), at 0.05° step size and 4 seconds step time. The diffractometer employed radiation from a Cu anode (1.54 Å) at 40 kV 40 mA. A 1 mm divergence slit was used with the incident beam along with 0.12 mm soller slits in the diffracted beam path. A sodium iodide scintillation detector was used. The XRPD analyses were conducted under ambient laboratory conditions.

Example 2

An in-vivo exposure test was conducted after dosing different formulations of 120 mg of Compound (1) sodium salt in dogs (n=6). Formulations A-F above were tested (see FIG. 2). The mean plasma concentration in serum of the dogs was assessed over time. Tablets containing Compound (1) in amorphous form were able to achieve improved in-vivo exposure in dogs compared to the crystalline form.

Figure 2:
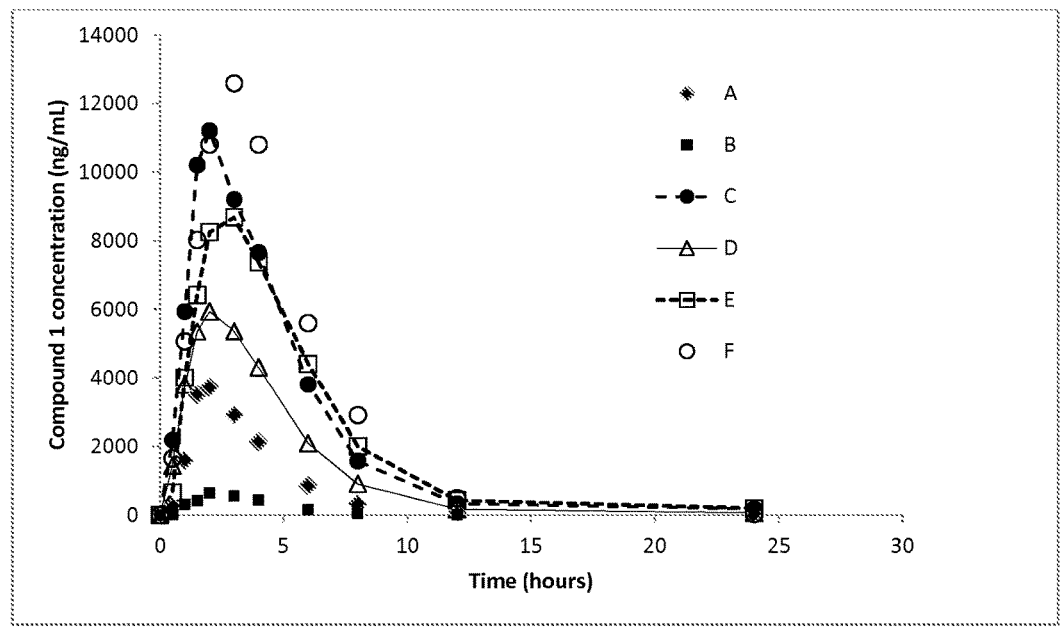
FIG. 2 shows the results of in-vivo exposure tests conducted after dosing tablet (A-E) and soft-gel (F) formulations of 120 mg of Compound (1) in dogs, the A-F formulations are described below.

The two amorphous forms which showed the highest in-vitro dissolution also resulted in >70% exposure relative to liquid filled softgel capsule, as shown in FIG. 2. While the crystalline drug formulations achieved only 20% or less exposure relative to liquid filled softgel capsule, two out of three amorphous formulations achieved >70% exposure relative to liquid filled softgel capsule.

Example 3

Dosage forms of Compound (1) were monitored for Compound X degradant formation during a storage test. The dosage forms according to the invention are Formulations G and H shown below. These were compared against the above-described known liquid in soft-gel capsule form of the drug, Formulation F.

Tablet formulations G and H were prepared, respectively, using the active as an amorphous solid or in an amorphous solid dispersion with arginine in a process including granulating, blending and tableting. The amorphous Compound (1) sodium salt (Formulation G) or the amorphous dispersion of the active in arginine (Formulation H) are prepared by dissolving the active in the organic solvent (Formulation G) or aqueous organic solvent (Formulation H) and then spray drying at a chosen inlet temperature and atomizer speed. It can be advantageous to conduct the granulating, blending and tableting processes in an environment which prevents moisture.

|  | Formulation G | Formulation H |
|---|---|---|
| Compound (1) - Na salt | 22.36 | 22.36 |
| SDS | 9.09 | 9.1 |
| Arginine | 22.36 | 19.5* |
| Mannitol | 40.36 | 24.2 |
| Croscarmellose sodium | 4.55 | 4.55 |
| Microcrystalline cellulose | 23.5 | 24.4 |
| Sodium stearyl fumarate | 1.27 | 0.50 |

*Part of this (9.6% of total tablet weight) of arginine added to active as solid dispersion.

Table 1 shows the results of the accelerated stability study of Compound X degradant formation in Formulations G and H. The tablets were stored in polypropylene bottles with dessicant at 4° C., 25° C., 30° C. and 40° C. Compound X levels in the tablets show little or no temperature dependence as compared to the softgel capsule. However, the soft gelatin capsule formulation shows a distinct temperature effect in formation of degradant X.

Compound X levels in Formulation F (softgel capsule) batches showed temperature dependence with higher levels at 25° C., 30° C. and 40° C. than when refrigerated.

The invention claimed is:
1. A solid oral dosage composition comprising:
Compound (1), or a pharmaceutically acceptable salt thereof, in the amorphous state:

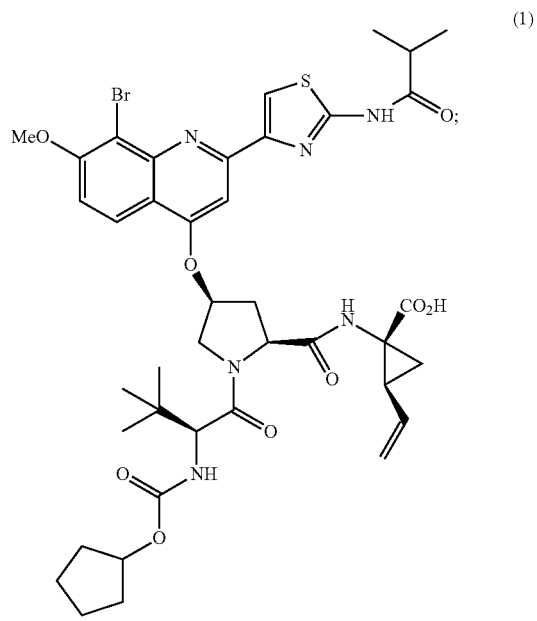 [SMILES: C=C[C@@H]1C[C@]1(NC(=O)[C@@H]1C[C@H](Oc2cc(-c3csc(NC(=O)C(C)C)n3)nc3c(Br)c(OC)ccc23)CN1C(=O)[C@@H](NC(=O)OC1CCCC1)C(C)(C)C)C(=O)O]

(1)

and
either a water-soluble base; or a hydrophilic, solid dispersion-forming polymer; or
both a water-soluble base and a hydrophilic, solid dispersion-forming polymer.

2. A solid oral dosage composition according to claim 1, which comprises a water-soluble base.

3. A solid oral dosage composition according to claim 1, which comprises a hydrophilic, solid dispersion-forming polymer.

4. A solid oral dosage composition according to claim 1, which comprises a water-soluble base and a hydrophilic, solid dispersion-forming polymer.

5. A solid oral dosage composition according to claim 3, wherein Compound (1), or a pharmaceutically acceptable

TABLE 1

Stability-improved formulations showing no temperature dependence of Compound X as compared to capsule formulation.

| | | | Timepoint | | | | | |
|---|---|---|---|---|---|---|---|---|
| | | | T = 2 mo | | | T = 3 mo | | |
| Storage condition | T = 0 | 4° C. | 25° C. 60% RH | 30° C. 65% RH | 40° C. 75% RH | 4° C. | 25° C. 60% RH | 30° C. 65% RH | 40° C. 75% RH |
| | | | Compound X (ppm) | | | | | |
| Formulation G | 1.2 | 1.0 | 1.3 | 1.2 | 1.7 | 0.7 | 0.7 | 1.0 | 1.8 |
| Formulation H | 0.7 | 1.1 | 1.1 | 0.8 | 0.9 | <QL | 0.6 | 0.6 | 0.6 |

QL: Quantification level salt thereof, in the amorphous state is in the form of an amorphous solid dispersion in the polymer.

6. A solid oral dosage composition according to claim 1, further comprising a surfactant.

7. A solid oral dosage composition according to claim 1, in the form of a tablet.

8. A solid oral dosage composition according to claim 1, in the form of a powder.

9. A solid oral dosage composition according to claim 1, which is storage stable at room temperature.

10. The solid oral dosage composition according to claim 1, wherein the water-soluble base is arginine, tromethamine, meglumine, carbonate buffer or sodium carbonate.

11. The solid oral dosage composition according to claim 1, wherein the water-soluble base is arginine.

12. The solid oral dosage composition according to claim 1, wherein the water-soluble base is dispersed with the Compound (1), or a pharmaceutically acceptable salt thereof, in the amorphous state.

13. The solid oral dosage composition according to claim 1, wherein the hydrophilic, solid dispersion-forming polymer is a polyvinylpyrrolidine or copolymer thereof or a cellulosic polymer.

14. The solid oral dosage composition according to claim 1, wherein the hydrophilic, solid dispersion-forming polymer is a polyvinylpyrrolidine.

15. The solid oral dosage composition according to claim 6, wherein the surfactant is an anionic surfactant.

16. The solid oral dosage composition according to claim 6, wherein the surfactant is selected from alkyl sulfates, alkyl ether sulfates, sulfonates, phosphates and carboxylates.

17. The composition of claim 1, wherein the amount of degradation product Compound X:

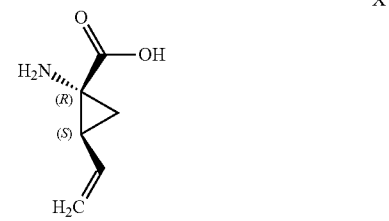

in the composition is below a level of about 400 µg when the composition contains a full daily dose of Compound (1) or pharmaceutically acceptable salt thereof in either single or multiple dosage units.

18. The solid oral dosage composition according to claim 6, wherein the surfactant is sodium dodecyl sulfate (SDS).

19. A solid oral dosage composition according to claim 4, wherein Compound (1), or a pharmaceutically acceptable salt thereof, in the amorphous state is in the form of an amorphous solid dispersion in the polymer.

* * * * *